United States Patent [19]

Sonoda

[11] Patent Number: 4,677,844
[45] Date of Patent: Jul. 7, 1987

[54] APPARENT VISCOSITY MEASURING APPARATUS

[75] Inventor: Noboru Sonoda, Ichihara, Japan

[73] Assignee: Idemitsu Kosan Company Limited, Tokyo, Japan

[21] Appl. No.: 780,471

[22] Filed: Sep. 26, 1985

[30] Foreign Application Priority Data

Oct. 17, 1984 [JP] Japan ................ 59-219270

[51] Int. Cl.$^4$ ........................................... G01N 11/04
[52] U.S. Cl. ................................................ 73/55; 73/54
[58] Field of Search .............................. 73/54, 55, 56

[56] References Cited

U.S. PATENT DOCUMENTS

| T869,014 | 12/1969 | Gray, Jr. et al. | 73/56 |
| 2,131,379 | 9/1938 | Lay | 73/55 |
| 3,535,917 | 10/1970 | Blair et al. | 73/55 |
| 3,895,513 | 7/1975 | Richardson | 73/55 |
| 3,990,295 | 11/1976 | Renovanz et al. | 73/55 |
| 4,539,837 | 9/1985 | Barnaby | 73/55 |

FOREIGN PATENT DOCUMENTS

| 2913652 | 10/1980 | Fed. Rep. of Germany | 73/55 |
| 109835 | 6/1983 | Japan | 73/55 |
| 587366 | 1/1978 | U.S.S.R. | 73/55 |

Primary Examiner—Stewart J. Levy
Assistant Examiner—Hezron E. Williams
Attorney, Agent, or Firm—Flynn, Thiel, Boutell & Tanis

[57] ABSTRACT

A measuring apparatus for conducting a method of testing an apparent viscosity of grease. In this apparatus, four capillary tubes are connected to a cylinder and these capillary tubes are selectively opened to atmosphere one after another by a switching mechanism. When a piston is pushed by pressure applied to hydraulic oil supplied to one chamber formed in the cylinder, the grease contained in the other chamber is pushed out through one of the capillary tubes and the pressure required for the push-out is detected by a sensor. This measurement is repeated with each of the capillary tubes.

5 Claims, 2 Drawing Figures

APPARENT VISCOSITY MEASURING APPARATUS

BACKGROUND OF THE INVENTION

1. Field of the Invention

This invention relates to an apparent viscosity measuring apparatus, and more particularly to an apparatus for conducting a method of testing an apparent viscosity.

2. Description of the Prior Art

An apparent viscosity of grease serves as one criteria when a pressure loss in a grease feed during a concentrated grease feed, performance of an initial torque or a running torque or a bearing and the like are evaluated.

As prescribed in JIS (Japanese Industrial Standard) K-2220 and ASTM-1092, this method of testing the apparent viscosity of grease is intended for that, when a cylinder connected thereto with capillary tubes is filled up with test grease and this test grease is pushed out of any one of the capillary tubes, pressure applied to the cylinder is measured to thereby seek the apparent viscosity of the test grease.

In this case, in general, several types of capillary tubes (four tubes, normally) different in diameter from one another are used on a test sample, and measurements are made with the shearing speed being changed.

However, only one capillary tube has been connected to a cylinder in the conventional measuring apparatus, thereby presenting the following disadvantages.

Namely, from necessity of conducting measurements by using several types of capillary tubes and changing the shearing speed, it is disadvantageous that capillary tubes should be exchanged one after another during measuring.

In general, since the cylinder is housed in a constant temperature bath and immersed in a heat transfer medium such as methanol so as to hold the temperature of grease at a predetermined temperature, the heat transfer medium must be discharged each time the capillary tube is exchanged, and moreover, a time duration required for conditioning the heat transfer medium received in the constant temperature bath again to the predetermined temperature is wasteful.

Further, in order to exchange the capillary tube without the discharge of the heat transfer medium from the constant temperature bath, it is necessary to take the cylinder out of the constant temperature bath, thus making the burden too heavy for a worker.

Anyway, with the conventional apparatus, in measuring one test sample, much time and labor have been required, the handling thereof has been extremely troublesome and the measuring efficiency has been very low.

When a test sample, a possible measured pressure of which is beyond imagination, is measured, a pressure gauge may have a scaleover to result in a failure in measurement, thus presenting such an inconvenience that a measurer should watch the apparatus during measuring and change over to a proper pressure gauge as necessary.

SUMMARY OF THE INVENTION

The present invention has as its object the provision of an apparent viscosity measuring apparatus capable of labor saving and automizing in measurement with no exchange of capillary tubes being required during measuring of an apparent viscosity of a test sample.

The present invention features that the apparatus is constituted by the following components.

A cylinder, in which a piston is inserted, and lid members are provided at opposite ends thereof respectively, whereby there are defined a first chamber for containing a test sample and a second chamber for containing hydraulic oil to push the piston;

means for feeding the hydraulic oil to the second chamber so as to push the piston toward the first chamber;

a plurality of capillary tubes each constructed such that one end thereof is secured to the lid member to be communicated with the first chamber and the other end is open to atmosphere, the capillary tubes having inner diameters being different from one another;

switching means for selectively opening the capillary tubes to atmosphere one after another; and means for measuring the pressure applied to the hydraulic oil when the grease is pushed out of the capillary tubes.

DETAILED DESCRIPTION OF THE PREFERRED EMBODIMENT

Description will hereunder be given of the embodiment of the present invention with reference to the drawings.

Figure 1:
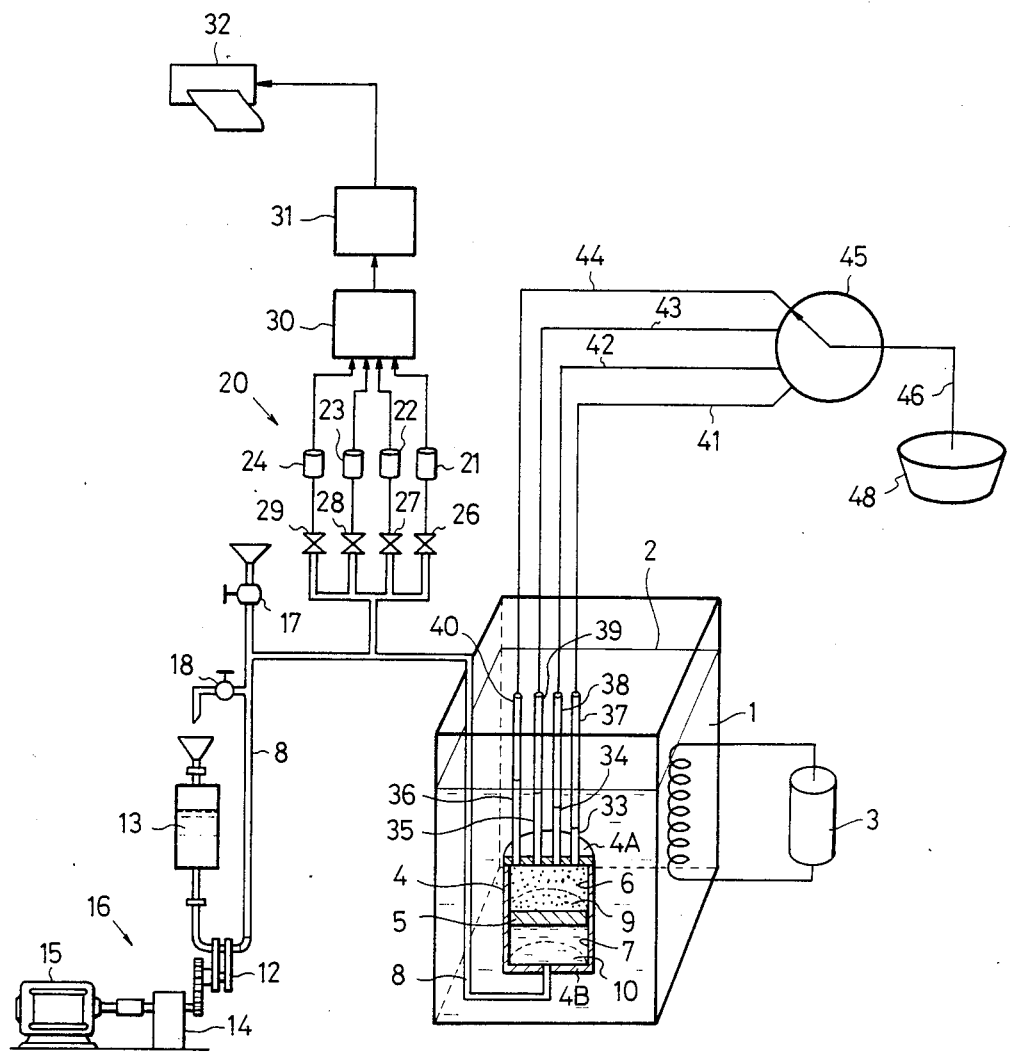
FIG. 1 is a schematic arrangement view, partially sectional, showing the general arrangement of one embodiment of the present invention.

In FIG. 1, a constant temperature bath 1 is filled up with a heat transfer medium 2 such as methanol and this heat transfer medium 2 is set to a predetermined temperature by temperature control means 3 such as a refrigeration machine.

A cylinder 4 formed at opposite ends thereof with lid members 4A and 4B is immersed in the heat transfer medium 2 in the constant temperature bath 1.

A piston 5 is water tightly and movably inserted into the cylinder 4, whereby a first chamber 6 and a second chamber 7 are defined. The first chamber 6 is filled up with grease 9 to be tested and the second chamber 7 is fed with hydraulic oil 10.

One end of a pressure pipe 8 for feeding the hydraulic oil 10 is connected to the lid member 4B on the side of the second chamber 7 and the other end is connected to a gear pump 12. This gear pump 12 is connected thereto with a hydraulic oil vessel 13 and adapted to be driven by a motor 15 through a reduction gear 14. Here, the pressure pipe 8, the gear pump 12, the hydraulic oil vessel 13, the reduction gear 14 and the motor 15 constitute hydraulic oil feeding means 16.

In the intermediate portion of the pressure pipe 8, there are provided a safety valve 17, a valve 18 for returning the hydraulic oil 10 to the hydraulic oil vessel 13, and pressure measuring means 20 for measuring the pressure applied to the hydraulic oil 10.

The pressure measuring means 20 includes four sensors 21, 22, 23 and 24, which are different in measuring range from one another. These sensors 21 to 24 are provided on four pipes forked from the pressure pipe 8, respectively. In the intermediate portions of these pipes, there are provided four valves 26, 27, 28 and 29. With the arrangement, data measured by the sensors 21 to 24 are delivered to an A/D converter 31 through a switching box 30. The measured data processed in a predetermined way in this A/D converter 31 is indicated by a printer 32.

On the other hand, connected to the lid member 4A of the first chamber 6 of the cylinder 4 are four capillary tubes 33, 34, 35 and 36 which are constructed according to the standards such as JIS and have inner diameters and lengths different from one another. These capillary tubes 33 to 36 are connected to a five-way exchange valve 45 as being the switching means through spaces 37, 38, 39 and 40, and pipes 41, 42, 43 and 44, respectively.

The valve 45, comprising an electrically driven rotary valve, for example, is adapted to selectively, switchingly communicate one end of a pipe 46 for discharging the grease 9 to a receiver 48 with any one of end portions of pipes 41 to 44 which are connected to the capillary tubes 33 to 36, respectively. In other words, when any one of the capillary tubes 33 to 36 is communicated with the pipe 46, communications between the capillary tubes other than the above and the pipe 46 are shut off. Furthermore, the other end of the pipe 46 is an end open to atmosphere, so that the grease pushed out can be poured into the receiver 48.

A description will now be given of the operation of this embodiment.

Firstly, the heat transfer medium 2 is discharged from the constant temperature bath 1 or the cylinder 4 itself is taken out of the heat transfer medium 2, the lid member 4A of the cylinder 4 is opened and the cylinder 4 is filled up with the grease 9 and closed, and subsequently, ends of the capillary tubes 33 to 36 on one side are set to the lid member 4A, respectively. In this case, ends of the capillary tubes 33 to 36 on the other side are connected to the valve 45 through the pipes 41 to 44.

In performing this operation, a setting must be made in accordance with the standards such as JIS, with care being taken not to permit bubbles to mix into the grease and so forth.

When the above-mentioned setting is completed by the method of discharging the heat transfer medium 2 from the constant temperature bath 1, the constant temperature bath 1 is filled up with the heat transfer medium 2, and the constant temperature bath 1 is set to the predetermined temperature by the temperature control means 3. However, when the above-mentioned setting is performed by the method of taking the cylinder 4 out of the heat transfer medium 2, temperature adjustment is rapidly performed because the heat transfer medium 2 is held substantially at the predetermined temperature.

Subsequently, the valve 45 is operated to select the capillary tube to be used for the first measurement, while, there is opened a valve associated with the sensor having the optimal measuring range to measure by use of the selected capillary tube, and the switching box 30, A/D converter 31 and printer 32 are brought into operating conditions.

Thereafter, when the motor 15 is operated to drive the gear pump 12 and the hydraulic oil 10 is fed to the second chamber 7, the piston 5 is pushed, whereby the grease is pushed out into the receiver 48 through the capillary tube thus selected.

Here, the pressure applied to the hydraulic oil 10 when the grease is pushed out is detected by the selected sensor, and data thus detected is recorded in the printer 32 through the switching box 30 and the A/D converter 31.

When the measurement of pressure of pushing out the test sample for one capillary tube is completed as described above, the valve 45 is switched to open the capillary tube to be used next. In this case, any one of the valves 26 to 29 is switched in association with the sensor having the optimal measuring range to be expected, to thereby make the above-mentioned measurement. Thereafter, measurements are performed by use of all of the capillary tubes 33 to 36, repeating the same measurement as described above.

The results of measurements obtained on all of the capillary tubes 33 to 36 can be inserted into predetermined formulate prescribed in the JIS and like so as to seek an apparent viscosity.

This embodiment described above can offer the following advantages.

Namely, heretofore, the fact has been that, upon measuring the pushing pressure of the grease on one capillary tube, the tube is replaced by another tube, and this operation should be repeated several times. Whereas, according to this embodiment, it suffices that four capillary tubes 33 to 36 are previously set and only the valve 45 is operated. In consequence, necessity for the work to extract the heat transfer medium 2 is eliminated, so that the measuring operation can be performed very easily and rapidly.

Since it is possible to select a proper sensor as commensurate to the pressure to be measured out of the sensors 21 to 24, a sensor having the highest measuring range is used firstly in measuring the test sample, a possible measured pressure of which is beyond imagination, and, in view of the result, a sensor having a measuring range lower than the above-mentioned one may be used as necessary, whereby there should be no possibility of scaleover of the meter, so that extremely accurate measurements can be performed.

Figure 2:
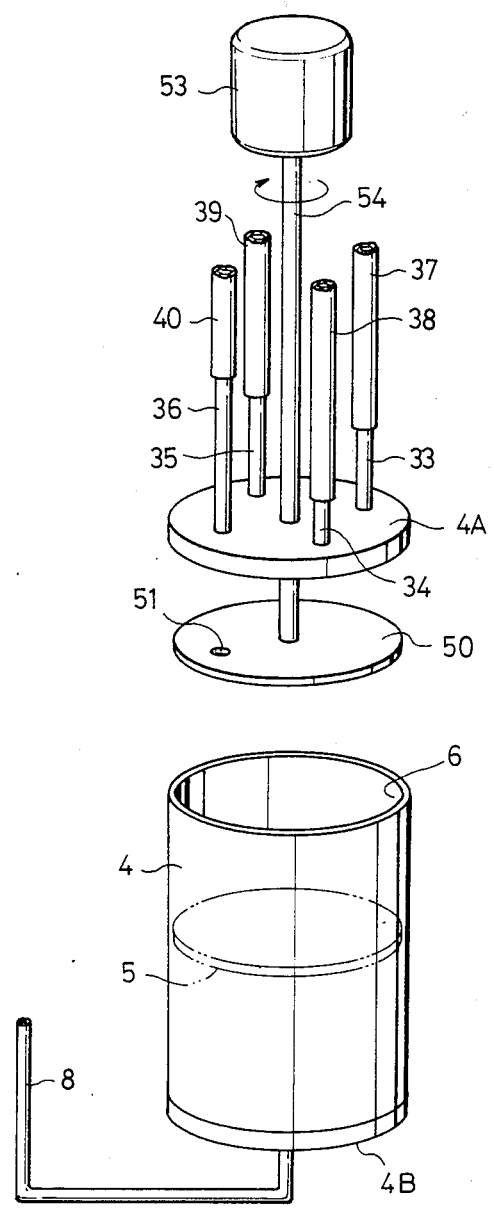
FIG. 2 is a disassembled perspective view showing a modification of the switching means used in the above embodiment.

In the above embodiment, description has been given of that, as the switching means, the five-way exchange valve 45 is adopted, however, the present invention need not necessarily be limited to this, and such a switching means may be adopted as being constituted by a switching disc 50 and a motor 53 for intermittently, rotatably driving this switching disc 50 as shown in FIG. 2 for example.

More specifically, the switching disc 50 is rotatably provided in the first chamber 6 of the cylinder 4 and provided with a hole 51 which selectively communicates end portions to be secured to the lid member 4A of the capillary tubes 33 to 36 with the interior of the first chamber 6. The switching disc 50 is connected at the central portion thereof with one end of an output shaft 54 of the motor 53, the output shaft 54 penetrating through the lid member 4A. Rotation of the motor 53 communicates any one of the capillary tubes 33 to 36 with the first chamber 6 of the cylinder 4, so that the opening of one of the capillary tubes to atmosphere can be selectively performed. Additionally, the capillary tubes 33 to 36 are secured to positions opposed to the position where the hole 51 of the switching disc 50 is formed, on a concentric circle on the lid member 4A.

In consequence, when the above-described switching means is used, such an advantage is added that the measured value can effectively avoid from being raised by a back pressure.

Further, in the foregoing explanation, the driving operations of the switching means and of the valves 26 to 29 for measuring the pressure are performed separately of each other, however, the former and the latter may be driven in association with each other by use of a known driving circuit. With this arrangement, the operations can be further simplified.

The switching means may use a solenoid valve. In this case, it suffices to use a circuit arrangement for controlling the opening or closing of the solenoid valve.

Further, the driving force of the switching disc 50 need not necessarily be limited to the motor, and a handle and the like for manual operation may be used, so that the construction can be simplified.

The switching means, the valves 26 to 29, the sensors 21 to 24, the switching box 30, the A/D converter 31, the printer 32 and the motor 15 are connected to a microcomputer through a known interface and the like, so that a series of operations of these members may be automatically performed. With this arrangement, all the measurements after the setting of the test sample, capillary tubes and the like can be automatically performed, so that the automizing and labor saving of the measurement can be achieved.

Further, the capillary tubes 33 to 36 have been different from one another, however, only if at least the inner diameters of the capillary tubes are different from one another, the capillary tubes may be lengths equal to one another.

As has been described hereinabove, the present invention can provide an apparent viscosity measuring apparatus wherein the test example is very easily and rapidly measured and the automizing and labor saving of the measurement can be achieved.

What is claimed is:

1. An apparent viscosity measuring apparatus wherein grease is pushed out under pressure through at least one capillary tube and the pressure applied to the grease during push-out is measured to thereby seek an apparent viscosity, comprising:

a cylinder, in which a piston is inserted, and lid members are provided at opposite ends thereof, respectively, whereby there are defined a first chamber for containing a test sample and a second chamber for containing hydraulic oil to push said piston;

means for feeding the hydraulic oil to said second chamber so as to push said piston toward said first chamber;

a plurality of capillary tubes each constructed such that one end thereof is secured to a first of said lid members to simultaneously provide communication between said first chamber and each of said capillary tubes, said capillary tubes each having a different inner diameter;

switching means for selectively opening a selected one of the other ends of said capillary tubes to atmosphere one after another; and means for measuring the pressure applied to the hydraulic oil when the grease is pushed out of said capillary tube, said pressure measuring devices, each having a different measuring range to thereby facilitate the selection of an appropriate pressure measuring device corresponding to the selected capillary tube to be used for measurement.

2. An apparent viscosity measuring apparatus as set forth in claim 1, wherein said switching means comprises a five-way exchange valve.

3. An apparent viscosity measuring apparatus as set forth in claim 1, wherein said switching means includes a switching disc rotatably provided in said cylinder and said switching disc is formed with a hole for providing communication between any one of said capillary tubes and said first chamber.

4. An apparent viscosity measuring apparatus as set forth in claim 3, wherein said switching disc is connected thereto with an output shaft of an intermittently drivable motor.

5. An apparent viscosity measuring apparatus as set forth in claim 1, wherein values measured by said pressure measuring means can be indicated by a printer.

* * * * *

UNITED STATES PATENT AND TRADEMARK OFFICE
CERTIFICATE OF CORRECTION

PATENT NO. : 4 677 844

DATED : July 7, 1987

INVENTOR(S) : Noboru Sonoda

It is certified that error appears in the above-identified patent and that said Letters Patent is hereby corrected as shown below:

```
Column 6, line 18; after "measuring" insert
        ---means including a plurality of pressure
            measuring---.
```

Signed and Sealed this

Nineteenth Day of January, 1988

Attest:

DONALD J. QUIGG

*Attesting Officer*  *Commissioner of Patents and Trademarks*